(12) United States Patent
Arora et al.

(10) Patent No.: US 11,607,178 B2
(45) Date of Patent: Mar. 21, 2023

(54) DRIFT, NOISE, AND MOTION ARTIFACT CORRECTION METHOD FOR PHOTOPLETHYSMOGRAM (PPG) SIGNALS AND SYSTEM THEREOF

(71) Applicant: SAMSUNG ELECTRONICS CO., LTD., Suwon-si (KR)

(72) Inventors: Rahul Arora, Kanpur (IN); Sujit Jos, Bangalore (IN); Ibrahim Abdul Majeed, Calicut (IN); Ka Ram Choi, Hwaseong-si (KR); Sang Kon Bae, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 359 days.

(21) Appl. No.: 16/828,364

(22) Filed: Mar. 24, 2020

(65) Prior Publication Data

US 2020/0323493 A1 Oct. 15, 2020

(30) Foreign Application Priority Data

Apr. 11, 2019 (IN) .............................. 201941014614
Feb. 6, 2020 (KR) ........................ 10-2020-0014244

(51) Int. Cl.
*A61B 5/00* (2006.01)
*A61B 5/024* (2006.01)
(Continued)

(52) U.S. Cl.
CPC ............ *A61B 5/7225* (2013.01); *A61B 5/021* (2013.01); *A61B 5/02416* (2013.01);
(Continued)

(58) Field of Classification Search
CPC ... A61B 5/7225; A61B 5/021; A61B 5/02416; A61B 5/7207; A61B 5/725
See application file for complete search history.

(56) References Cited

U.S. PATENT DOCUMENTS 7,035,679 B2 *  4/2006  Addison .............. A61B 5/6816
                                                          600/323
7,515,949 B2     4/2009  Norris
(Continued)

FOREIGN PATENT DOCUMENTS

KR          10-0721803 B1     5/2007
KR          10-1641024 B1     7/2016
KR       10-2018-0012891 A    2/2018

OTHER PUBLICATIONS

Lee, Han-Wook, et al. "The periodic moving average filter for removing motion artifacts from PPG signals." International Journal of Control, Automation, and Systems 5.6 (2007): 701-706. (Year: 2007).*

(Continued)

*Primary Examiner* — Navin Natnithithadha
*Assistant Examiner* — Meghan R Kumar
(74) *Attorney, Agent, or Firm* — Sughrue Mion, PLLC

(57) ABSTRACT

The present disclosure relates to a method and system for processing a photoplethysmogram (PPG) signal to improve accuracy of measurement of physiological parameters of a subject. The method may include removing a baseline drift from the PPG signal; obtaining a drift removed signal; filtering the drift removed signal; obtaining a filtered signal; performing motion artifact correction on the filtered signal; and obtaining a corrected signal.

20 Claims, 7 Drawing Sheets

(51) Int. Cl.
    *A61B 5/021* (2006.01)
    *A61B 5/145* (2006.01)
(52) U.S. Cl.
    CPC .......... *A61B 5/14532* (2013.01); *A61B 5/725* (2013.01); *A61B 5/726* (2013.01); *A61B 5/7207* (2013.01); *A61B 5/7296* (2013.01)

(56) References Cited

U.S. PATENT DOCUMENTS

| | | | |
|---|---|---|---|
| 7,620,450 B2 | 11/2009 | Kim et al. | |
| 8,364,225 B2* | 1/2013 | Addison | A61B 5/14551 600/336 |
| 8,498,696 B2 | 7/2013 | Yen et al. | |
| 2013/0080489 A1* | 3/2013 | Ochs | A61B 5/02416 708/201 |
| 2016/0361041 A1 | 12/2016 | Barsimantov et al. | |
| 2020/0178821 A1* | 6/2020 | Wu | A61B 5/721 |

OTHER PUBLICATIONS

Tang, SK Deric, et al. "PPG signal reconstruction using a combination of discrete wavelet transform and empirical mode decomposition." 2016 6th International Conference on Intelligent and Advanced Systems (ICIAS). IEEE, 2016. (Year: 2016).*

V Bhavana et al. "Feasibility of Authenticating Medical Data Using Photoplethysmography(ppg) as Signature Mark" International Journal of Advanced Research in Computer Science and Software Engineering, vol. 4, Issue 1, Jan. 2014, (pp. 635-641).

Chen Wei et al. "Study on conditioning and feature extraction algorithm of photoplethysmography signal for physiological parameters detection" Research gate, Oct. 2011, (5 pages total).

* cited by examiner

DRIFT, NOISE, AND MOTION ARTIFACT CORRECTION METHOD FOR PHOTOPLETHYSMOGRAM (PPG) SIGNALS AND SYSTEM THEREOF

CROSS-REFERENCE TO RELATED APPLICATION(S)

This application is based on and claims priority under 35 U.S.C. § 119 to Indian Patent Application No. 201941014614, filed on Apr. 11, 2019, in the Indian Patent Office, and to Korean Patent Application No. 10-2020-0014244, filed on Feb. 6, 2020, in the Korean Intellectual Property Office, the disclosures of which are incorporated by reference herein in their entireties.

BACKGROUND

1. Field

Embodiments of the present disclosure are generally related to signal processing, and are more particularly related to a method and system of processing a photoplethysmogram (PPG) signal to improve accuracy of measurement of physiological parameters of a subject.

2. Description of Related Art

Photoplethysmogram (PPG) is an optical technique used to measure blood volume changes in a microvascular bed of tissues. The PPG technique is often used to make measurements at a skin surface by using a pulse oximeter which illuminates skin and measures changes in light absorption. The PPG technique is a non-invasive and inexpensive technique used to measure blood pressure, heart rate, and oxygen saturation, glucose levels, and mental stress levels. However, the PPG technique may be affected by artifacts such as motion artifacts, baseline drift, and high frequency noise. All the mentioned artifacts affect accuracy of the PPG signal measurement.

Thus, the accuracy of measurement may be improved by removing baseline drift, high frequency noise, and a motion artifact from the PPG signal.

SUMMARY

Additional aspects will be set forth in part in the description which follows and, in part, will be apparent from the description, or may be learned by practice of the presented embodiments.

According to an aspect of the disclosure, a method for processing a photoplethysmogram (PPG) signal includes removing, by a device, a baseline drift from the PPG signal; obtaining, by the device, a drift removed signal, based on removing the drift from the PPG signal; filtering, by the device, the drift removed signal; obtaining, by the device, a filtered signal, based on filtering the drift removed signal; performing, by the device, motion artifact correction on the filtered signal; and obtaining, by the device, a corrected signal, based on performing the motion artifact correction on the filtered signal.

According to an aspect of the disclosure, a system for processing a photoplethysmogram (PPG) signal includes a memory that may store instructions; and a processor that may execute the instructions to remove a baseline drift from the PPG signal; obtain a drift removed signal, based on removing the baseline drift from the PPG signal; filter the drift removed signal; obtain a filtered signal, based on filtering the drift removed signal; perform motion artifact correction on the filtered signal; and obtain a corrected signal, based on performing the motion artifact correction on the filtered signal.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
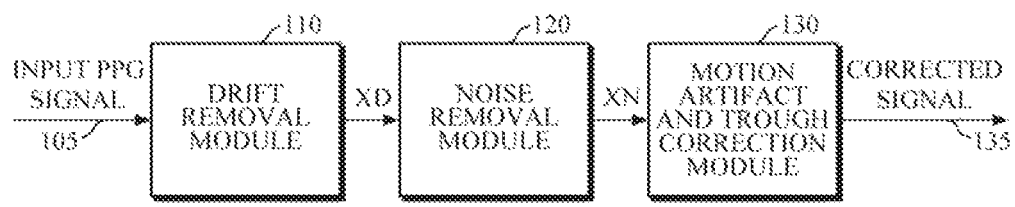
FIG. 1 illustrates a block diagram of a PPG signal correction system according to an embodiment.

In the present disclosure, the term "exemplary" is used herein to mean "serving as an example, instance, or illustration." Any embodiment or implementation of the present disclosure described herein as "exemplary" is not necessarily to be construed as preferred or advantageous over other embodiments.

While the disclosure is susceptible to various modifications and alternative forms, specific embodiments thereof are shown by way of example in the drawings and will be described in detail below. It should be understood that the present disclosure is not limited to the disclosure to the particular forms disclosed, and that the disclosure is to cover all modifications, equivalents, and alternatives within the spirit and the scope of the disclosure.

The terms "comprises," "comprising," or any other variations thereof, are intended to cover a non-exclusive inclusion, such that a setup, device, or method that comprises a list of components or steps might not include only those components or steps but may include other components or steps not expressly listed or inherent to such setup or device or method. In other words, one or more elements in a device or system or apparatus proceeded by "comprises . . . a" does not, without more constraints, preclude the existence of other elements or additional elements in the device or system or apparatus.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1 illustrates a block diagram of a PPG signal correction system according to an embodiment.

As shown in FIG. 1, the PPG signal correction system comprises a drift removal module 110, a noise removal module 120, and a motion artifact and trough correction module 130. The drift removal module 110 includes a plurality of sub-modules to remove a baseline drift from an input PPG signal 105. The plurality of sub-module uses a discrete wavelet transform (DWT) to remove the baseline drift from the input PPG signal. The noise removal module 120 filters a drift removed signal using one or more filters. The motion artifact and trough correction module 130 processes the filtered signal using a continuous wavelet transform (CWT) to obtain a corrected PPG signal 135.

Figure 2:
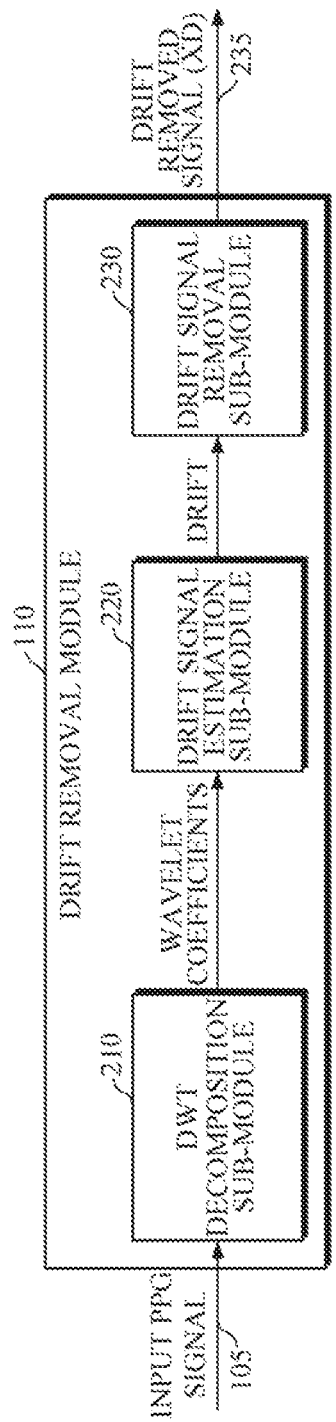
FIG. 2 illustrates a block diagram of a drift removal module of the system according to an embodiment.

FIG. 2 illustrates a block diagram of the drift removal module of the system according to an embodiment.

As shown in FIG. 2, the drift removal module 110 includes a discrete wavelet transform (DWT) decomposition sub-module 210, a drift signal estimation sub-module 220, and a drift signal removal sub-module 230. The drift removal module 110 uses DWT for removing the baseline drift from the input PPG signal 105.

The DWT decomposition sub-module 210 performs a multi-level decomposition on the input PPG signal 105 using DWT to obtain approximated coefficients ($a_M$) and detailed coefficients ($d_M$).

In general, discrete wavelet transform (DWT) is expressed as shown below in equation 1.

$$Xw(j,k) = \int_{-\infty}^{\infty} x(t) \frac{1}{\sqrt{2^j}} \psi\left(\frac{t - 2^j k}{2^j}\right) dt \quad \text{Eq. (1)}$$

where 'j' is the scaling parameter, and 'k' is the translation parameter.

In the DWT decomposition sub-module 210, the input PPG signal 105 is decomposed using DWT to yield approximated and detailed coefficients. The approximated coefficients are represented as $a_1, a_2, \ldots a_M$ and the detailed coefficients are represented as $d_1, d_2, \ldots d_M$. In an embodiment, the approximated coefficients are obtained by using an inner product of the input PPG signal 105 and $\phi_{M,n}(t)$, and the detailed coefficients are obtained by using an inner product of the input PPG signal 105 and $\psi_{M,n}(t)$ as shown in equation 2.

$$a_M(n) = \langle x(t), \phi_{M,n}(t) \rangle, d_M(n) = \langle x(t), \psi_{M,n}(t) \rangle \quad \text{Eq. (2)}$$

wherein, $$\psi_{m,n}(t) = 2^{-\frac{m}{2}} \psi(2^{-m}t - n) \quad \text{Eq. (3)}$$

$$\phi_{m,n}(t) = 2^{-\frac{m}{2}} \phi(2^{-m}t - n) \quad \text{Eq. (4)}$$

where m is the scaling parameter, n is the translation parameter, $\psi(t)$ is the mother wavelet, and $\phi(t)$ is the father wavelet.

The drift signal estimation sub-module 220 obtains a drift signal from the approximated coefficients. At any predefined level M, the approximated and detailed coefficients generated using the DWT decomposition sub-module 210 are used to obtain an approximated signal ($A_M$) and a detailed signal ($D_M$), respectively, as shown below in equation 5. The approximated signal is the estimate of the low varying drift signal.

$$A_M = \sum_{n=-\infty}^{+\infty} a_M(n)\phi_{M,n}(t), D_M = \sum_{n=-\infty}^{+\infty} d_M(n)\psi_{M,n}(t) \quad \text{Eq. (5)}$$

The drift signal removal sub-module 230 obtains a drift removed signal by removing the drift signal from the input PPG signal 105. In an embodiment, the DWT decomposition is performed using Daubechies 4 (db4) as a mother wavelet and the drift signal is obtained using a $9^{th}$ level approximation coefficient ($a_9$). The drift signal (A9) is then removed from the input PPG signal as shown in equation 6 to obtain the drift removed signal.

Drift removed signal($X_D$)=Input PPG signal−Drift Signal($A9$)      Eq. (6)

Figure 3A:
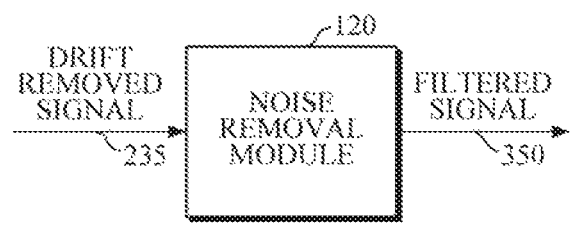
FIG. 3A illustrates a block diagram of a noise removal module of the system according to an embodiment.

FIG. 3A illustrates a block diagram of a noise removal module of the system according to an embodiment.

As shown in FIG. 3A, the noise removal module 120 filters the drift removed signal ($X_D$) 235 using a filter of order n to remove high frequency noise interference. The order of the filter n may be 2, 3, 5, 7, etc. The output from the drift removal module 110 is passed through the noise removal module 120 to remove a high frequency noise interference from the drift removed signal 235, and to capture viable information in the PPG signal 105. The choice of the frequency range and the order the of filter used in the noise removal module 120 is configured so as to preserve the viable information in PPG signal 105. In an exemplary embodiment, to preserve viable information in the PPG signal 105, the frequency band of 0.04 to 30 Hz is selected. In an embodiment, the filter is a Butterworth filter. In another embodiment, the filter is Chebyshev filter. In an embodiment, the noise removal module 120 includes a plurality of filters to remove high frequency noise interference from the input PPG signal 105.

Figure 3B:
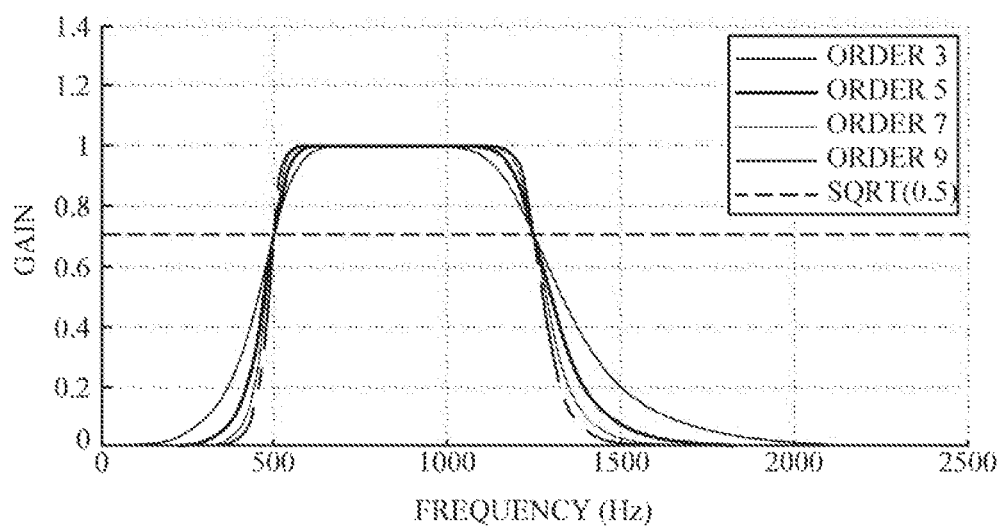
FIG. 3B illustrates a frequency response of a Butterworth filter with different orders according to an embodiment.

FIG. 3B illustrates an exemplary embodiment of a frequency response of a Butterworth filter according to an embodiment.

As shown in FIG. 3B, the plot depicts a frequency response of a Butterworth filter of different orders to an input signal. The noise outside a selected frequency band is removed by the filter, and the filter preserves viable information of the PPG signal 105. In an embodiment, the filter configured in the noise removal module 120 is a Butterworth filter of order 4. The choice of the order of the filter and the frequency band of the filter is configured so as to preserve the essential information in PPG signal 105.

Figure 4:
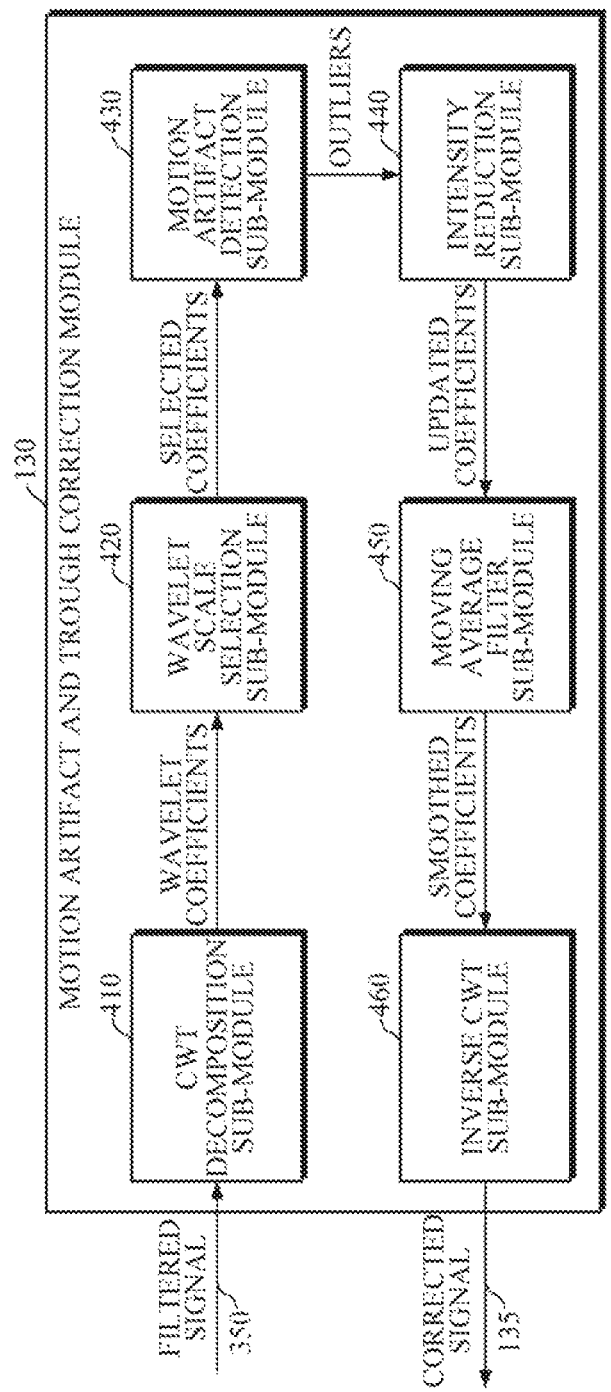
FIG. 4 illustrates a block diagram of a motion artifact and trough correction module of the system according to an embodiment.

FIG. 4 illustrates a block diagram of a motion artifact and trough correction module of the system according to an embodiment.

As shown FIG. 4, the motion artifact and trough correction module 130 includes a Continuous Wavelet Transform (CWT) decomposition sub-module 410, a wavelet scale selection sub-module 420, a motion artifact detection sub-module 430, an intensity reduction sub-module 440, a moving average filter sub-module 450, and an Inverse CWT (ICWT) sub-module 460.

The CWT decomposition sub-module 410 performs a decomposition on the filtered signal 350 to obtain a plurality of wavelet coefficients using CWT.

In general, the continuous wavelet transform (CWT) of function is expressed as shown below in equation 7:

$$X_w(s, \tau) = \frac{1}{|s|^{1/2}} \int_{-\infty}^{\infty} x(t) \overline{\psi}\left(\frac{t - \tau}{s}\right) dt \quad \text{Eq. (7)}$$

where τ is the translation parameter, "s" is the scaling parameter, and $\psi(t)$ is the mother wavelet.

The wavelet scale selection sub-module 420 select the range of "s" to obtain a wavelet scalogram (energy distribution) for the selected coefficients. In an embodiment, a wavelet scalogram represents the energy percentage of each wavelet coefficient. In an embodiment, the value of "s" is in the range of 20 to 36.

The motion artifact detection sub-module 430 identifies motion artifact corrupted coefficients from the selected coefficients as outliers. The selected coefficients are identified as outliers based on the energy percentage of the selected coefficients being greater than a threshold for the same translation parameter and more than two scaling parameters. For each value of "s," mean and standard deviation of energy across translation parameters is computed. In an embodiment, the threshold is configured to be three standard deviations from the mean.

The intensity reduction sub-module 440 corrects the identified outliers by reducing the intensity of the selected wavelet coefficients. In an embodiment, for each value of "s," intensity reduction is performed by computing the mean and the standard deviation of the non-corrupted coefficients, and updating motion artifact corrupted coefficients as shown in equation 8.

$$\text{updated\_motion artifact corrupted\_coefficients} = \text{motion artifact corrupted\_coefficients} * \frac{\text{not\_motion artifact corrupted\_mean}}{\text{not\_motion artifact corrupted\_std}} \quad \text{Eq. (8)}$$

The moving average filter sub-module 450 filters all of the wavelet coefficients to obtain smoothed coefficients. In an embodiment, the moving average filter is a simple low pass finite impulse response (FIR) filter of a predefined window size applied to all of the wavelet coefficients as shown in equation 9. The window size can be selected based on the scenario. The smoothed coefficients obtained from the moving average filter sub-module 450 are trough corrected coefficients.

$$Y[i] = \frac{1}{M} \sum_{k=-(M-1)/2}^{(M-1)/2} X[i+k] \quad \text{Eq. (9)}$$

wherein 'M' represents the window size.

The inverse CWT sub-module 460 reconstructs the PPG signal from the smoothed coefficients using an inverse continuous wavelet transform (ICWT) as shown in equation 10. In an embodiment, the Morlet wavelet is used as a mother wavelet for reconstruction of the corrected PPG signal 135.

$$x(t) = \frac{1}{C_\psi} \int_s \int_\tau <x(t), \psi_{s,\tau}(t)> \psi_{s,\tau}(t) d\tau \frac{ds}{s^2} \quad \text{Eq. (10)}$$

wherein 'M' represents the window size.

Figure 5:
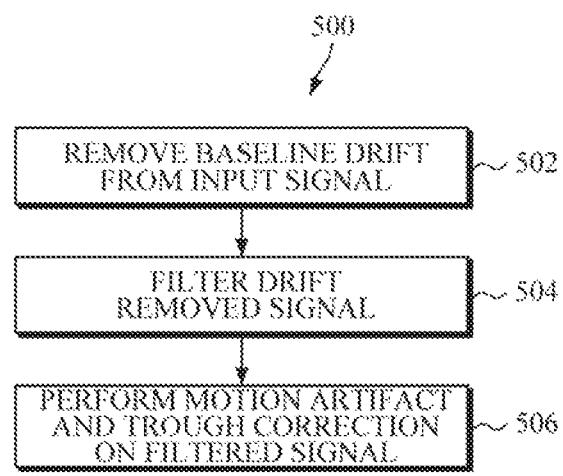
FIG. 5 illustrates a flowchart illustrating a method of correcting a PPG signal according to an embodiment.

FIG. 5 shows a flowchart illustrating a method of correcting a PPG signal according to an embodiment. The example flow diagram may include one or more operations as illustrated by blocks 502-506, which represent operations that may be performed in a method by functional modules in a device.

In FIG. 5, blocks 502-506 are illustrated as being performed sequentially, with block 502 being performed first and block 506 being performed last. It will be appreciated however that these blocks may be re-arranged as convenient to suit particular embodiments and that these blocks or portions thereof may be performed concurrently in some embodiments. It will also be appreciated that in some examples various blocks may be eliminated, divided into additional blocks, and/or combined with other blocks.

At a "remove baseline drift from input signal" block 502, a baseline drift from an input signal is removed. The removal of the baseline drift from an input PPG signal 105 includes performing a multi-level decomposition on the input PPG signal 105 using discrete wavelet transform (DWT) to obtain a detailed coefficiency and an approximated coefficient. In an embodiment, the approximated coefficients are obtained by using $\phi_{M,n}(t)$ and the detailed coefficients are obtained by using $\psi_{M,n}(t)$. The removal of baseline drift from the input PPG signal 105 further includes obtaining a drift signal from the approximated coefficients at a pre-defined level. In an embodiment, the pre-defined level is 9. The drift signal is obtained from the approximated coefficient. The removal of baseline drift from an input PPG signal 105 further includes removing the drift signal from the input signal to obtain a drift removed signal 235.

At a "Filter drift removed signal" block 504, the drift removed signal 235 is filtered to obtain a filtered signal 350. Filtering of the drift removed signal 235 is performed by using a filter of order n, and the order of the filter n may be 2, 3, 5, 7, etc. The choice of the frequency range and the order of the filter used in the noise removal module 120 is configured so as to preserve the viable information in PPG signal 105. In an embodiment, to preserve viable information in PPG signal 105 the frequency band of 0.04 to 30 Hz is selected.

At a "Perform motion artifact and trough correction on filtered signal" block 506, the motion artifact correction is performed on the filtered signal 350 to obtain corrected signal 135.

In an embodiment, performing motion artifact correction includes decomposing the filtered signal 350 to obtain a plurality of wavelet coefficients using CWT, and selecting the range of scale "s" to obtain a wavelet scalogram (energy distribution) for the selected coefficients. In an embodiment, wavelet scalogram represents the energy percentage of each wavelet coefficient. In one embodiment, the value of "s" is in the range of 20 to 36.

In an embodiment, performing motion artifact correction further includes identifying motion artifact corrupted coefficients from the selected coefficients as outliers. The selected coefficients are identified as outliers based on the energy percentage of the selected coefficients being greater than a threshold for the selected coefficients with the same translation parameter value and more than two scaling parameters. For each value of "s," the mean and the standard deviation of energy across translation parameters is determined. In an embodiment, the threshold is configured to be three standard deviations from the mean.

In an embodiment, performing motion artifact correction further includes correcting the identified outliers by reducing the intensity of the selected wavelet coefficients, filtering the updated outlier coefficients to obtain smoothed coefficients, and passing the smoothed coefficients through an ICWT to reconstruct the corrected PPG signal.

Thus, the present disclosure improves accuracy of the photoplethysmogram (PPG) signal by removing baseline drift and high frequency noise from the PPG signal. The present disclosure also improves accuracy of the PPG signal by correcting the trough and motion artifacts in the PPG signals.

Figure 6:
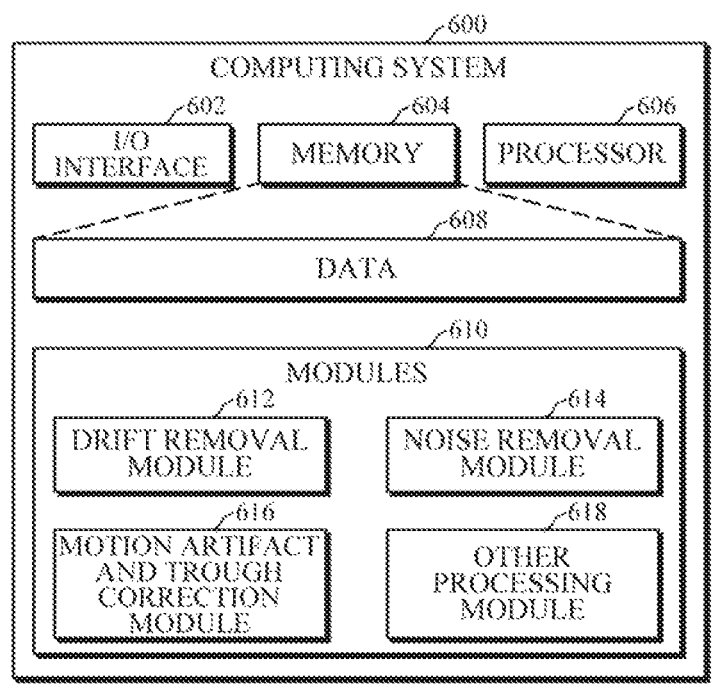
FIG. 6 illustrates a block diagram of a computing system according to an embodiment.

FIG. 6 illustrates a block diagram of a computing system according to an embodiment of the disclosure.

The computing system 600 may include an input/output (I/O) interface 602, a memory 604, and at least one central processing unit ("CPU" or "processor") 606.

The I/O interface 602 is coupled with the processor 606 through which an input signal and/or an output signal is received/transmitted.

The memory 604 may include a volatile memory (such as random access memory (RAM)), a non-volatile memory (such as read-only memory (ROM), flash memory, etc.), or any combination thereof. The memory 604 stores one or more instructions executable by the at least one processor 606, and is communicatively coupled to the processor 606. The one or more data 608 may be stored within the memory 604. The one or more data 608 includes approximated and detailed coefficients data, drift signal data, mean data, and standard deviation data of wavelet coefficients.

The processor 606 is configured to process a photoplethysmogram (PPG) signal to improve accuracy of the PPG signal based on the data 608 stored in the memory 604. The processor 606 may be of any type including, but not limited, to a microprocessor (µP), a microcontroller (µC), a digital signal processor (DSP), or any combination thereof. Processor 606 may include one or more levels of caching, such as a level one cache and a level two cache, a processor core, and registers. The processor core may include an arithmetic logic unit (ALU), a floating-point unit (FPU), or any combination thereof.

The one or more data 608 in the memory 604 is processed by modules 610 of the processor 606. The modules 610 includes a drift removal module 612, a noise removal module 614, and a motion artifact and trough correction module 616, and other processing module 618. The drift removal module 612 is configured to remove a baseline drift from an input PPG signal 105 to obtain a drift removed signal. The noise removal module 614 is configured to filter the drift removed signal to obtain a filtered signal. The motion artifact and trough correction module 616 is configured to perform motion artifact correction on the filtered signal to obtain a corrected signal. In an exemplary embodiment, the computing system 600 may be a medical device.

The language used in the present disclosure has been principally selected for readability and instructional purposes, and it might not have been selected to delineate or circumscribe the subject matter. It is therefore intended that the scope of the present disclosure not be limited by the present disclosure. Accordingly, the present disclosure is intended to be illustrative, but not limiting, of the scope of the claimed subject matter.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A method for processing a photoplethysmogram (PPG) signal, the method comprising:
    removing, by a device, a baseline drift from the PPG signal;
    obtaining, by the device, a drift removed signal, based on removing the drift from the PPG signal;
    filtering, by the device, the drift removed signal;
    obtaining, by the device, a filtered signal, based on filtering the drift removed signal;
    performing, by the device, motion artifact correction on the filtered signal, wherein the performing the motion artifact correction comprises:
        obtaining a plurality of wavelet coefficients by applying a continuous wavelet transform (CWT) to the filtered signal;
        identifying motion artifact corrupted coefficients from the plurality of wavelet coefficients, as outliers, based on an energy percentage of the plurality of wavelet coefficients being greater than a threshold for a same translation parameter and more than two scaling parameters; and
        updating the motion artifact corrupted coefficients by reducing an intensity of the identified motion artifact corrupted coefficients; and
    obtaining, by the device, a corrected signal, based on the updated motion artifact corrupted coefficients.

2. The method of claim 1, further comprising:
    measuring at least one of a blood pressure, a heart rate, an oxygen saturation, a glucose level, and a mental stress level based on the corrected signal.

3. The method of claim 1, wherein removing the baseline drift from the PPG signal comprises:
    performing a multi-level decomposition on the PPG signal using discrete wavelet transform (DWT);
    obtaining approximation coefficients, based on performing the multi-level decomposition on the PPG signal;
    obtaining a drift signal from the approximation coefficients at a pre-defined level;
    removing the drift signal from the PPG signal; and
    obtaining the drift removed signal based on removing the drift signal from the PPG signal.

4. The method of claim 1, wherein the plurality of wavelet coefficients comprise approximated coefficients and detailed coefficients, and
    wherein the approximated coefficients are obtained by using an inner product of the filtered signal of the PPG signal and a father wavelet, and the detailed coefficients are obtained by using an inner product of the filter signal of the PPG signal and a mother wavelet.

5. The method of claim 1, wherein filtering the drift removed signal is performed by using a filter of order n, and wherein the order of the filter n is 2, 3, 5, or 7.

6. The method of claim 5, wherein the filter is at least one of a Butterworth filter, a Type-I Chebyshev filter, and a Type-II Chebyshev filter.

7. The method of claim 5, further comprising:
    selecting a frequency band of the filter to retain a maximum energy and viable information in the drift removed signal, wherein the frequency band ranges from 0.04 hertz (Hz) to 30 Hz.

8. The method of claim 1, wherein performing the motion artifact correction on the filtered signal further comprises:
    applying a moving average filter (MAF) on the plurality of wavelet coefficients;
    obtaining smoothed coefficients, based on applying the MAF on the plurality of wavelet coefficients; and
    reconstructing the corrected signal from the smoothed coefficients using an inverse continuous wavelet transform (ICWT).

9. The method of claim 8, wherein identifying the motion artifact corrupted coefficients comprises:
    identifying the motion artifact corrupted coefficients based on obtaining a wavelet scalogram from the wavelet coefficients.

10. The method of claim 8, wherein the intensity is reduced using a mean and a standard deviation of non-corrupted wavelet coefficients.

11. A system for processing a photoplethysmogram (PPG) signal, the system comprising:
a memory configured to store instructions; and
a processor configured to execute the instructions to:
remove a baseline drift from the PPG signal;
obtain a drift removed signal, based on removing the baseline drift from the PPG signal;
filter the drift removed signal;
obtain a filtered signal, based on filtering the drift removed signal;
perform motion artifact correction on the filtered signal by
obtaining a plurality of wavelet coefficients by applying a continuous wavelet transform (CWT) to the filtered signal;
identifying motion artifact corrupted coefficients from the plurality of wavelet coefficients, as outliers, based on an energy percentage of the plurality of wavelet coefficients being greater than a threshold for a same translation parameter and more than two scaling parameters; and
updating the motion artifact corrupted coefficients by reducing an intensity of the identified motion artifact corrupted coefficients; and
obtain a corrected signal, based on the updated motion artifact corrupted coefficients.

12. The system of claim 11, wherein the processor is further configured to:
measure at least one of a blood pressure, a heart rate, an oxygen saturation, a glucose level, and a mental stress level based on the corrected signal.

13. The system of claim 11, wherein the processor is configured to:
perform a multi-level decomposition on the PPG signal using a discrete wavelet transform (DWT);
obtain approximation coefficients, based on performing the multi-level decomposition on the PPG signal;
obtain a drift signal from the approximation coefficients at a pre-defined level;
remove the drift signal from the PPG signal; and
obtain the drift removed signal, based on removing the drift signal from the PPG signal.

14. The system of claim 13, wherein the multi-level decomposition is performed by using a Daubechies 4 (db4) mother wavelet.

15. The system of claim 11, wherein filtering of the drift removed signal is performed by use of a filter of order n, and wherein the order of the filter n is 2, 3, 5, or 7.

16. The system of claim 15, wherein the filter is at least one of a Butterworth filter, a Type-I Chebyshev filter, and a Type-II Chebyshev filter.

17. The system as claimed in claim 15, wherein the processor is further configured to:
select a frequency band of the filter to retain a maximum energy and viable information in the drift removed signal, and wherein the frequency band ranges from 0.04 hertz (Hz) to 30 Hz.

18. The system of claim 11, wherein the processor is configured to perform motion artifact correction on the filtered signal by
applying a moving average filter (MAF) on the plurality of wavelet coefficients;
obtaining smoothed coefficients, based on applying the MAF on the plurality of wavelet coefficients; and
reconstructing the corrected signal from the smoothed coefficients using an inverse continuous wavelet transform (ICWT).

19. The system of claim 18, wherein the processor is configured to identify the motion artifact corrupted coefficients by obtaining a wavelet scalogram from the wavelet coefficients.

20. The system of claim 18, wherein the intensity is reduced using a mean and a standard deviation of non-corrupted coefficients.

\* \* \* \* \*